United States Patent [19]

Ransford

[11] Patent Number: 5,043,492

[45] Date of Patent: Aug. 27, 1991

[54] METHOD FOR PRODUCING HEXABROMOCYCLODODECANE

[75] Inventor: George H. Ransford, Magnolia, Ark.

[73] Assignee: Ethyl Corporation, Richmond, Va.

[21] Appl. No.: 569,867

[22] Filed: Aug. 20, 1990

[51] Int. Cl.$^5$ .................. C07C 17/02; C07C 22/00
[52] U.S. Cl. .................................................. 570/186
[58] Field of Search ........................................ 570/186

[56] References Cited

U.S. PATENT DOCUMENTS

| | | | |
|---|---|---|---|
| 3,544,641 | 12/1970 | Versnel | 260/648 |
| 3,558,727 | 1/1971 | Jenkner et al. | 260/648 |
| 3,652,688 | 3/1972 | Olechowski et al. | 260/648 |
| 3,833,675 | 9/1974 | Newcombe et al. | 260/648 |
| 4,783,563 | 11/1988 | Taniuchi et al. | 570/186 |
| 4,918,253 | 4/1990 | Hermolin et al. | 570/231 |

FOREIGN PATENT DOCUMENTS

| | | | |
|---|---|---|---|
| 0037895 | 10/1981 | European Pat. Off. | 570/186 |
| 0181414 | 5/1986 | European Pat. Off. | 570/186 |
| 3120621 | 9/1982 | Fed. Rep. of Germany | 570/186 |
| 3447631 | 7/1989 | Fed. Rep. of Germany | 570/186 |
| 505187 | 2/1975 | Japan | 570/186 |

OTHER PUBLICATIONS

"Azeotropic and Extractive Distillation", Kirk-Othmer Encyclopedia of Chemical Technology, Third Edition, Suppl. Volume, 1984, pp. 145-158.

Primary Examiner—Werren B. Lone
Attorney, Agent, or Firm—David E. LaRose

[57] ABSTRACT

A process for obtaining an improved yield of hexabromocyclododecane by utilizing a solvent in the reaction mass containing a minor amount of water.

8 Claims, No Drawings

METHOD FOR PRODUCING HEXABROMOCYCLODODECANE

BACKGROUND

This invention relates to a process for obtaining an improved yield of a product predominant in hexabromocyclododecane.

Methods of bromination of cyclododecatriene (e.g. trans, trans, trans-, or trans, trans, cis-1,5,9-cyclododecatriene or mixtures thereof) in solvent(s) to produce hexabromocyclododecane (HBCD) are known. For examples of prior art teaching bromination of cyclododecatriene to produce HBCD in solvent media of lower alcohols (i.e. $C_1$–$C_4$) and/or halogenated hydrocarbons, see U.S. Pat. Nos. 3,558,727 (Jenkner et al.) and 3,833,675 (Newcombe et al.). After the bromination reaction, the reaction mass can be subjected to separation techniques (e.g. filtration, centrifugation, or decantation) to produce a recovered mass, which is predominantly HBCD particles but which can additionally contain contaminants to this product, and to recover the solvent for reuse. For examples of such techniques, see U.S. Pat. No. 3,558,727 (Jenkner et al.) and U. K. 2,205,830 (Hermolin et al.). The use of a relatively higher alcohol (i.e. $C_4$–$C_8$) solvent media is taught in U.S. Pat. No. 4,783,563 (Tanuichi et al.) but only in conjunction with a catalytic complex (i.e. boron trifluoride complex). There continues to be a need for a solvent media which not only produces relatively pure HBCD, but also results in an increased yield of useable product.

THE INVENTION

This invention relates to a process for the production of a product predominant in hexabromocyclododecane (HBCD) the process comprising brominating cyclododecatriene in a $C_3$–$C_8$ alcohol solvent containing from about 2 to about 5 weight percent water such that an increased yield of the hexabromocyclododecane product is obtained.

The process of this invention not only provides an increased yield of HBCD product but leads to simplification of the solvent recovery system which in turn reduces the operating costs of the process. These and other advantages are evident from the ensuing description.

In another embodiment, this invention provides a process for the production of a product predominant in hexabromocyclododecane, the process comprising: (a) brominating cyclododecatriene in a solvent comprising isobutanol and from about 2 to about 5 weight percent water such that the increased yield of the product predominant in hexabromocyclododecane is obtained; (b) separating the product from the solvent as a first wet cake; (c) neutralizing the first wet cake with a basic solution; (d) subsequent to neutralization, recovering a second wet cake; and (e) drying the second wet cake to obtain the product predominant in hexabromocyclododecane.

In producing HBCD, cyclododecatriene may be brominated by a variety of well known techniques. One such technique is the bromination of cyclododecatriene disclosed in Jenkner et al. U.S. Pat. No. 3,558,727 incorporated herein by reference. The cyclododecatriene which is brominated may be trans, trans, trans- or trans, trans, cis-1,5,9-cyclododecatriene or mixtures thereof (hereinafter referred to as CDT).

At process initiation, the solvent is charged to the reaction vessel. The solvent preferably contains a minor amount of water, e.g. from about 2 to about 5 weight percent of the total solvent used. To obtain the desired amount of water in the solvent, water can be admixed with the solvent, before, during, or after charging the solvent to the reaction vessel. In a highly preferred embodiment, solvent containing water from a previous batch of HBCD is dried until the solvent contains the desired amount of water, then the solvent is recycled for use in a subsequent batch of HBCD. For the first batch of HBCD, water is admixed with the solvent prior to performing the bromination reaction.

In one embodiment of the invention, the solvent is a $C_3$–$C_8$ alcohol. In a more preferred embodiment the solvent is a $C_4$–$C_5$ alcohol and most preferably the solvent is isobutanol.

After production of the HBCD, the solvent can be collected and recycled to the reaction vessel after drying the solvent to the desired degree. Once the HBCD product is removed from the solvent, the solvent is neutralized with an aqueous basic solution such as $Na_2CO_3$, $NaOH$, $KOH$, $NH_4OH$ and the like. Preferably an amount of $Na_2CO_3$ solution is used to neutralize the solvent such that a pH of from about 6 to about 8 and most preferably a pH of from about 6.8 to about 7.2 is obtained. The pH of the solvent is not critical to the invention as the pH is a function of the materials of construction for the solvent drying and handling equipment.

Since water is added to the solvent with the aqueous basic solution during the neutralization of the solvent, additional water need not be added to the reaction vessel if recycle solvent is used. However, the solvent which has been neutralized may contain too much water. Thus a solvent drying system is preferably used in order to provide suitable solvent for recycle and further HBCD production.

In the solvent drying system, the neutralized solvent is separated into an organic phase and an aqueous phase. The organic phase which contains a minor amount of water is heated and a vapor having an aqueous portion and an organic portion is recovered as a condensate. The organic portion containing an amount of dissolved water is then contacted with a substantially dry vapor stream in a stripping operation to remove essentially all of the water from the organic phase. By adjusting the operation parameters within the drying system, a wet solvent having from about 3 to about 4 percent water can be obtained.

When isobutanol is used as the solvent, it has been found that considerable cost savings can be achieved by heating a mixture initially containing isobutanol and water, collecting the overhead vapors as a condensate, separating an isobutanol phase from an aqueous phase in the condensate, and returning the isobutanol phase having an amount of dissolved water to be removed to the top of the stripping column. The isobutanol phase is then contacted with an essentially water-free isobutanol vapor in a counter-current stripping operation to remove substantially all of the water from the isobutanol phase. The essentially water-free isobutanol vapor can be obtained by continuing to heat the mixture which mixture initially contains isobutanol and water, until essentially water-free isobutanol vapors are generated. Since isobutanol boils at a higher temperature than water and/or the isobutanol/water mixture, dry or essentially water-free isobutanol vapors can be generated for use as a stripping medium. During contact with the essentially water-free isobutanol vapors, water is removed from the isobutanol phase. By adjusting the flow of vapor and/or the isobutanol phase, the amount of water in stripped solvent can be adjusted within a range of from less than about 1 weight percent water to more than about 6 weight percent water.

The pressure utilized in the solvent drying system is not critical to the operation. Thus pressures from subatmospheric to superatmospheric may be used. Performing the vaporization and stripping operations at atmospheric pressure is preferable due to the less costly equipment design.

Once the reaction vessel is charged with the solvent, containing a minor amount of water, addition of the bromine and CDT to the reaction vessel can be initiated. A sufficient amount of bromine is utilized such that substantially all of the CDT is brominated to hexabromocyclododecane. Stoichiometrically three moles of bromine are required for each mole of CDT to be brominated. Preferably the reaction vessel is charged with a minor amount of bromine prior to initiating the co-feed of CDT and bromine. This minor amount of bromine provides an excess of from about 1 to about 6 percent of the stoichiometric quantity of bromine required to obtain the desired hexabromocyclododecane predominant product. This excess amount of bromine is maintained during and subsequent to the addition of bromine and CDT to the reaction vessel.

Preferably the CDT and bromine are co-fed to the reaction vessel at spatially separate locations. And most preferably, both the bromine and CDT are charged to the reaction vessel such that they are introduced into the vessel below the liquid level of solvent and reactants in the vessel.

During the addition of the CDT and bromine, the temperature of the reaction mass thus formed rises from about 10° C. to about 40° C. or higher due to the heat of reaction. It is desirable to maintain the reaction mass at a temperature of from about 30° C. to about 50° C. during the co-feed addition of bromine and CDT. Since the bromination of CDT is an exothermic reaction, cooling may be required to maintain the temperature of the reaction mass in the desired range.

During the addition of the co-feed of CDT and bromine, the vessel is agitated sufficiently to provide contact between the reactants and good heat transfer. When about one-half of the CDT has been fed to the reaction vessel, the agitation is decreased to about one-half of the initial agitation rate. The degree of agitation should be sufficient to provide for heat transfer and contact between the reactants without resulting in HBCD particle breakage or degradation.

To provide a stirrable reaction mass, it is desirable to utilize enough solvent considering the amount of HBCD being produced. In terms of the amount of HBCD being produced, it is preferable to utilize an amount of solvent substantially equal in weight to the amount of HBCD product. More or less solvent can be used in accordance with the particular equipment selection.

As the HBCD particles form, they precipitate from the reaction mass. This precipitate is a mixture of alpha, beta, and gamma isomers of HBCD with the gamma isomer being the most desirable. It has been discovered that by using a solvent containing from about 3 to about 5 weight percent water, the solubility of HBCD isomers in the solvent can be decreased. This decrease in solubility leads to an increase in the recovery of HBCD from the reaction mass. If the solvent contains too much water, however, a gummy product is formed which is much more difficult to filter. If the solvent is too dry, the yield of recoverable product is reduced.

To purify and collect the HBCD product, conventional means are used. The reaction mass is permitted to cool to ambient temperature. Cooling can be done with an induced cooling rate of about 45° C. per minute. Preferably, cooling to a temperature of no more than about 40° C. The reaction mass can then be subjected to conventional separation techniques (e.g. filtration, centrifugation or decantation) to recover solid particles from the reaction mass. Such separations in accordance with the embodiments of the invention can effect a preferential recovery of the higher melting point particles by utilizing the differences existing in the size and mass of the isomer particles.

Washing of the separated HBCD particles can be effected by the techniques known to those in the art. Illustrative of these methods include rinsing the filtrate on a centrifuge or filter with water. Alternatively, separated particles can be slurried in a solvent or water and subsequently filtered.

The wet cake containing the HBCD particles is then dried at a temperature above about 70° C. Preferably, the temperature for drying is in the range of from about 75° to about 120° C. and most preferably, the temperature is in a range of from about 80° to about 110° C.

The following examples illustrate one or more embodiments of the invention, but are not intended to limit the invention to a particular set of parameters.

EXAMPLE

CDT was brominated generally in accordance with the technique of U.S. Pat. No. 3,558,727 (Jenkner et al.). An amount of solvent was used so as to provide a theoretical loading of 50% HBCD particles in the solvent. A molar excess of 4% bromine was maintained throughout the bromination. Isobutanol was used as the solvent. The amount of water in the solvent in each run was indicated in the Table. A centrifuge was used to separate the HBCD product from the solvent. The increase in the amount of recovered HBCD particles was evidenced by the amount of residue remaining in the centrifuge. As the residue decreased, the yield of HBCD product increased.

TABLE

| HBCD Batch | $H_2O$ in IBA wt % | Residue wt % |
|---|---|---|
| 1 | 0.96 | 18.0 |
| 2 | 0.74 | 18.3 |
| 3 | 2.90 | 9.8 |
| 4 | 3.0 | 3.6 |
| 5 | 1.4 | 5.2 |
| 6 | 1.6 | 10.2 |

Variations in the process of this invention are within the spirit and scope of the appended claims.

I claim:

1. A process for producing an increased yield of a product predominant in hexabromocyclododecane (HBCD), said process comprising brominating cyclododecatriene with bromine in a $C_3$–$C_4$ alcohol solvent containing from about 2 to about 5 weight percent water such that said increased yield is obtained.

2. The process of claim 1 wherein the solvent is predominantly isobutanol.

3. The process of claim 1 wherein the bromination is conducted at a temperature ranging from about 10° C. to about 50° C.

4. The process of claim 1 wherein the yield of HBCD ranges from about 90 percent to about 98 percent of theoretical.

5. A process for producing an increased yield of a product predominant in hexabromocyclododecane, said process comprising:
 a) brominating cyclododecatriene with bromine in a solvent comprising isobutanol, and from about 2 to about 5 weight percent water such that said increased yield of the product predominant in hexabromocyclododecane is obtained,
 b) separating said product from the solvent as a first wet cake;
 c) neutralizing the first wet cake with a basic solution;
 d) subsequent to neutralization, recovering a second wet cake; and
 e) drying the second wet cake to obtain the product predominant in hexabromocyclododecane.

6. The process of claim 5 wherein the bromination is conducted at a temperature ranging from about 10° C. to about 50° C.

7. The process of claim 6 wherein the product is dried at a temperature ranging from about 80° C. to about 110° C.

8. The process of claim 7 wherein the yield of HBCD ranges from about 90 percent to about 98 percent of theoretical.

* * * * *